(12) United States Patent
Paramasivan et al.

(10) Patent No.: US 12,099,690 B2
(45) Date of Patent: Sep. 24, 2024

(54) SYSTEMS AND METHODS FOR GENERATING DYNAMIC GRAPHICAL USER INTERFACES FOR MONITORING AND CONTROLLING CONNECTED DEVICES

(71) Applicant: Stryker Corporation, Kalamazoo, MI (US)

(72) Inventors: Ramanan Paramasivan, San Jose, CA (US); Brandon B. Hunter, Hollister, CA (US); Rohit P. Godhani, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/658,091

(22) Filed: Apr. 5, 2022

(65) Prior Publication Data

US 2022/0317827 A1    Oct. 6, 2022

Related U.S. Application Data

(60) Provisional application No. 63/170,915, filed on Apr. 5, 2021.

(51) Int. Cl.
*G06F 3/0481* (2022.01)
*A61B 34/00* (2016.01)
*G06F 3/04847* (2022.01)

(52) U.S. Cl.
CPC ........... *G06F 3/0481* (2013.01); *A61B 34/25* (2016.02); *G06F 3/04847* (2013.01); *A61B 2034/256* (2016.02); *A61B 2034/258* (2016.02)

(58) Field of Classification Search
CPC ...... G06F 3/0481; G06F 3/04847; G06F 8/65; G06F 8/451; G06F 9/4413; G06F 9/4415;
(Continued)

(56) References Cited

U.S. PATENT DOCUMENTS

| 6,556,219 B1 | 4/2003 | Wugofski | |
|---|---|---|---|
| 2003/0141987 A1* | 7/2003 | Hayes | H04B 1/205 340/12.25 |

(Continued)

OTHER PUBLICATIONS

International Search Report and Written Opinion mailed Jun. 30, 2022, directed to International Application No. PCT/US2022/023454; 16 pages.

*Primary Examiner* — Jennifer N Welch
*Assistant Examiner* — Ashley M Fortino
(74) *Attorney, Agent, or Firm* — Morrison & Foerster LLP

(57) ABSTRACT

Presented herein are systems and methods for dynamically updating and rendering graphical user interfaces at a surgical hub device that is configured to simultaneously coordinate the operation of multiple medical devices connected to the hub. According to an aspect, when a device is connected to the hub, the device can send identifying information to the hub so that the hub can ascertain the identity of the device. Based on the identification data, the hub can access an internal graphical user interface (GUI) database to determine if there are any entries in the database that correspond to the device that is now connected to the hub. If it is determined that the internal GUI database of the hub contains one or more GUIs associated with the device, then the GUI database can transmit the corresponding to GUIs to the electronic display for rendering at the appropriate times.

33 Claims, 7 Drawing Sheets

(58) Field of Classification Search
CPC .............. A61B 34/25; A61B 2034/256; A61B 2034/258; G16H 40/20; G16H 40/67
See application file for complete search history.

(56) References Cited

U.S. PATENT DOCUMENTS

| | | |
|---|---|---|
| 2019/0125454 A1 | 5/2019 | Stokes et al. |
| 2020/0042149 A1* | 2/2020 | Hatambeiki ........... G08C 17/02 |
| 2022/0104814 A1* | 4/2022 | Shelton, IV ......... A61B 17/072 |

* cited by examiner

SYSTEMS AND METHODS FOR GENERATING DYNAMIC GRAPHICAL USER INTERFACES FOR MONITORING AND CONTROLLING CONNECTED DEVICES

CROSS-REFERENCE TO RELATED APPLICATIONS

This application claims the benefit of U.S. Provisional Application No. 63/170,915, filed Apr. 5, 2021, the entire contents of which are hereby incorporated by reference herein.

FIELD

The present disclosure relates to the process of rendering graphical user interfaces on an electronic display operated by an electronic device configured to communicatively couple and operate one or more medical devices used during a surgical procedure.

BACKGROUND

Surgical procedures generally involve the use of multiple devices that aid the surgeon in performing the procedure. Each device used by the surgeon can provide its own information or data that may need to be visualized by the surgeon during a procedure. When surgeons need to view multiple sources of information, such as image data from different types of imaging tools, or measurement data from various surgical tools, the surgeons may have to either switch the input of their primary surgical display between the various image feeds or graphical user interfaces provided by each device so that they can interact with each of them when needed or manage multiple graphical user interfaces on separate screens simultaneously. The options can cause the surgeons to either to have constantly switch video inputs on a single display, or monitor multiple screens which may be located at different locations in the operation room. Thus, both options can significantly increase the cognitive burden experienced by the surgeon, which can increase the potential for errors to occur during the surgery.

Rather than operating multiple devices simultaneously and separately, a surgeon can employ a "hub" device that can interface with each and every device and allow the surgeons to control the multiple devices using one or more graphical user interfaces presented to the surgeon on a single electronic display without having to manually switch in the input feed to the electronic display. Using a hub, the surgeon can navigate the graphical user interfaces associated with each device connected to the hub on a single display, and can switch between graphical user interfaces associated with each device without having to manually change the video input feed of the display.

In one or more examples, the hub can store the graphical user interfaces associated with each device that can be connected to the hub, and then render those graphical user interfaces onto the electronic display at appropriate times or when called upon by the surgeon to do so. The graphical user interface can be stored on the memory of the hub, and when the hub detects that a particular device is connected to the hub, the hub can access the corresponding graphical user interfaces associated with the detected device at the memory and display the graphical user interface on the display at the appropriate time. In addition to graphical user interfaces, the hub can also store data associated with controlling the hub and can transmit commands from the surgeon (provided by the surgeon's interaction with a graphical user interface) to the device and can transmit data from the device to the surgeon via the electronic display. Thus, the hub can play a central role in the information flow between a surgeon and the devices used during the surgery.

Given its central role, and the danger associated with its failure, the hub may have to go through the same regulatory approval processes that other medical devices go through before they are allowed to be employed in an operating room. This regulatory process can be long and can often delay the time it takes for the hub to be deployed in an operating room to control the devices used during a surgery. The regulatory process for certifying that a hub can be used in an operating room can also apply to the software that the hub uses to render the graphical user interfaces for each device and to allow for the surgeon to communicate with the devices, since failure of the software itself can also lead to errors during the surgery. Thus, not only does the hub and its software have to undergo an initial regulatory approval process before being deployed in an operating room, but the software also has to go through the same process each time the software is updated to ensure that it complies with various safety rules and regulations.

Conventionally, the data and logic associated with the graphical user interfaces of each device that can connect to the hub is hard coded within the control system software of the hub. Thus, if a new device is launched later after the initial release of the control system, the graphical user interfaces associated with the new device will not be supported by the existing software stored on the hub. Thus, in order to accommodate a new device, the control system software of the hub will need to be updated to include built-in support for the newly released device. However, in order to update software, the new software update will have to go through the same regulatory process to verify and validate the software before the software update can be loaded onto each individual hub. In an environment where new devices can come online frequently, having to update the software and re-verify it can be a time and labor intensive process.

SUMMARY

According to an aspect, when a device is connected to the hub, the device can send identifying information to the hub so that the hub can ascertain the identity of the device. Based on the identification data, the hub can access an internal graphical user interface (GUI) database to determine if there are any entries in the database that correspond to the device that is now connected to the hub. If it is determined that the internal GUI database of the hub contains one or more GUIs associated with the device, then the GUI database can transmit the corresponding GUI(s) to the electronic display for rendering at the appropriate times (for instance when the surgeon issues a command at the hub to show the GUI associated with the device). However, if the internal GUI database does not include one or more GUIs associated with the device, then the hub can transmit a request to an external GUI database (that is e.g. located on a cloud computing device) to download one or more GUIs associated with the device being connected to the hub. the, e.g. cloud-based, external GUI database can be updated to include GUI information for new devices as they become available, and the external GUI database can thus serve a central repository for GUI information for devices that can be accessed by multiple hubs. the, e.g. cloud-based, GUI database can be updated by an external device that is communicatively coupled to the, e.g. cloud-based, GUI database. When a hub requests GUI information (such as GUI layout information) from the cloud-based GUI database, the database can search for corresponding entries, and transmit those entries to the requesting hub. The hub after receiving the GUI layout information from the cloud-based GUI database, can use the received information to update its own internal GUI database, and can also use the information to render GUIs for the new device. In this way, rather than requiring the hub to update its entire software to accommodate new devices, the hub can instead retrieve the new GUI information from the cloud-based GUI database without the need to update its software.

According to an aspect, a new device that is connected to the hub can be pre-loaded with its own GUI layout information. When the new device is connected to the hub for the first time, the device can for example, e.g. automatically, transmit its GUI layout information to the hub. The hub can receive this GUI layout information and store the information in its own internal GUI database. Thus, anytime the device is connected to the hub, the hub will already contain the necessary GUI information needed to render GUIs that correspond to that device at an electronic display for access and interaction by the surgeon performing a medical procedure.

According to an aspect, a method for controlling a surgical device connected to a surgical controller/hub includes: receiving data from a surgical device communicatively coupled to the controller, identifying the surgical device based on the received data, querying a database stored in a memory of the controller to determine if the database includes graphical user interface (GUI) layout information associated with the identified surgical device, wherein the GUI comprises graphical controls specific to the connected surgical device, if the memory does not include GUI layout information associated with the identified surgical device: transmitting a request to an external device for the GUI layout information associated with the identified device, receiving the requested GUI layout information from the external device, updating the database stored in the memory of the controller with the received GUI layout information, and rendering a GUI at the electronic display based on the received GUI layout information from the external device.

Optionally, the data received from the surgical device communicatively coupled to the controller comprises version information associated with software running on the surgical device.

Optionally, the database comprises a plurality of entries associated with the surgical device, wherein each entry of the database is associated with a version of the software running on the surgical device.

Optionally, the GUI layout information comprises information associated with a location on the electronic display of one or more graphical features to be displayed when operating the device associated with the GUI layout information, i.e. information associated with a location on the electronic display where the one or more graphical features are to be displayed when operating the device associated with the GUI layout information.

Optionally, the GUI layout information comprises information associated with one or more graphical features configured to accept input from a user of the surgical device associated with the GUI layout information.

Optionally, the GUI layout information includes a layout file.

Optionally, the layout file is implemented using JavaScript Object Notation (JSON) format.

Optionally, the layout file is implemented using Extensible Markup Language (XML) format.

Optionally, the GUI layout information includes a library file.

Optionally, the library file is implemented using a Dynamic-link library (DLL).

Optionally, the library file is implemented using statically linked library.

Optionally, the external device is implemented on a cloud-based computing device.

Optionally, the external device includes a GUI layout information database.

Optionally, the received requested GUI layout information is associated with the surgical device communicatively coupled to the controller.

Optionally, the GUI layout information database of the external device comprises information associated with a location on the electronic display of one or more graphical features to be displayed when operating the surgical device associated with the GUI layout information.

According to an aspect, a method for operating and maintaining a graphical user interface (GUI) layout database comprises: receiving GUI layout information from a first external device, wherein the GUI layout information comprises identification data that identifies one or more surgical devices associated with the GUI layout information, updating the GUI layout database with the received GUI layout information from the external device, receiving a request for GUI layout information from a second external device, wherein the received request includes surgical device identifying information matching the received surgical device identifying information to one or more entries in the GUI layout database, and transmitting the one or more matching entries in the GUI layout database to the second external device, wherein the second external device is configured to render one or more GUIs in response to determining that it is communicatively coupled to the surgical device, and wherein the GUI is rendered based on the transmitted one or more matching entries in the GUI layout database.

Optionally, the GUI layout information is received from the first external device over a network interface.

Optionally, the GUI layout information comprises information associated with one or more graphical features configured to accept input from a user of a surgical device associated with the GUI layout information.

Optionally, the GUI layout information includes a layout file.

Optionally, the layout file is implemented using JavaScript Object Notation (JSON) format.

Optionally, the layout file is implemented using Extensible Markup Language (XML) format.

Optionally, the GUI layout information includes a library file.

Optionally, the library file is implemented using a Dynamic-link library (DLL).

Optionally, the library file is implemented using a statically linked library.

Optionally, the second external device comprises a controller configured to control and coordinate one or more surgical device used during a surgical procedure.

According to an aspect, a system for controlling a surgical device connected to a surgical controller/hub includes: a memory, one or more processors, wherein the memory stores one or more programs that when executed by the one or more processors, cause the one or more processors to:

receive data from a surgical device communicatively coupled to the controller, identify the surgical device based on the received data, query a database stored in a memory of the controller to determine if the database includes graphical user interface (GUI) layout information associated with the identified surgical device, wherein the GUI comprises graphical controls specific to the connected surgical device, if the memory does not include GUI layout information associated with the identified surgical device: transmit a request to an external device for the GUI layout information associated with the identified device, receive the requested GUI layout information from the external device, update the database stored in the memory of the controller with the received GUI layout information, and render a GUI at the electronic display based on the received GUI layout information from the external device.

Optionally, the data received from the surgical device communicatively coupled to the controller comprises version information associated with software running on the surgical device.

Optionally, the database comprises a plurality of entries associated with the surgical device, wherein each entry of the database is associated with a version of the software running on the surgical device.

Optionally, the GUI layout information comprises information associated with a location of one or more graphical features to be displayed on the electronic display when operating the device associated with the GUI layout information.

Optionally, the GUI layout information comprises information associated with one or more graphical features configured to accept input from a user of the surgical device associated with the GUI layout information.

Optionally, the GUI layout information includes a layout file.

Optionally, the layout file is implemented using JavaScript Object Notation (JSON) format.

Optionally, the layout file is implemented using Extensible Markup Language (XML) format.

Optionally, the GUI layout information includes a library file.

Optionally, the library file is implemented using a Dynamic-link library (DLL).

Optionally, the library file is implemented using statically linked library.

Optionally, the external device is implemented on a cloud-based computing device.

Optionally, the external device includes a GUI layout information database.

Optionally, the received requested GUI layout information is associated with the surgical device communicatively coupled to the controller.

Optionally, the GUI layout information database of the external device comprises information associated with a location of one or more graphical features to be displayed on the electronic display when operating the surgical device associated with the GUI layout information.

According to an aspect, a system for operating and maintaining a graphical user interface (GUI) layout database includes: a memory, one or more processors, wherein the memory stores one or more programs that when executed by the one or more processors, cause the one or more processors to: receive GUI layout information from a first external device, wherein the GUI layout information comprises identification data that identifies one or more surgical devices associated with the GUI layout information, update a GUI layout database with the received GUI layout information from the external device, receive a request for GUI layout information from a second external device, wherein the received request includes surgical device identifying information, match the received surgical device identifying information to one or more entries in the GUI layout database, and transmit the one or more matching entries in the GUI layout database to the second external device, wherein the second external device is configured to render one or more GUIs in response to determining that it is communicatively coupled to the surgical device, and wherein the GUI is rendered based on the transmitted one or more matching entries in the GUI layout database.

Optionally, the GUI layout information is received from the first external device over a network interface.

Optionally, the GUI layout information comprises information associated with one or more graphical features configured to accept input from a user of a surgical device associated with the GUI layout information.

Optionally, the GUI layout information includes a layout file.

Optionally, the layout file is implemented using JavaScript Object Notation (JSON) format.

Optionally, the layout file is implemented using Extensible Markup Language (XML) format.

Optionally, the GUI layout information includes a library file.

Optionally, the library file is implemented using a Dynamic-link library (DLL).

Optionally, the library file is implemented using a statically linked library.

Optionally, the second external device comprises a controller configured to control and coordinate one or more surgical device used during a surgical procedure.

According to an aspect is provided a computer program product, or a non-transitory computer readable storage medium storing one or more programs, comprising software code portions for controlling a surgical device connected to a surgical controller/hub, for execution by one or more processors of an electronic device that when executed by the device, causes the device to: receive data from a surgical device communicatively coupled to the controller, identify the surgical device based on the received data, query a database stored in a memory of the controller to determine if the database includes graphical user interface (GUI) layout information associated with the identified surgical device, wherein the GUI comprises graphical controls specific to the connected surgical device, if the memory does not include GUI layout information associated with the identified surgical device: transmit a request to an external device for the GUI layout information associated with the identified device, receive the requested GUI layout information from the external device, update the database stored in the memory of the controller with the received GUI layout information, and render a GUI at the electronic display based on the received GUI layout information from the external device.

Optionally, the data received from the surgical device communicatively coupled to the controller comprises version information associated with software running on the surgical device.

Optionally, the database comprises a plurality of entries associated with the surgical device, wherein each entry of the database is associated with a version of the software running on the surgical device.

Optionally, the GUI layout information comprises information associated with a location of one or more graphical features to be displayed on the electronic display when operating the device associated with the GUI layout information.

Optionally, the GUI layout information comprises information associated with one or more graphical features configured to accept input from a user of the surgical device associated with the GUI layout information.

Optionally, the GUI layout information includes a layout file.

Optionally, the layout file is implemented using JavaScript Object Notation (JSON) format.

Optionally, the layout file is implemented using Extensible Markup Language (XML) format.

Optionally, the GUI layout information includes a library file.

Optionally, the library file is implemented using a Dynamic-link library (DLL).

Optionally, the library file is implemented using statically linked library.

Optionally, the external device is implemented on a cloud-based computing device.

Optionally, the external device includes a GUI layout information database.

Optionally, the received requested GUI layout information is associated with the surgical device communicatively coupled to the controller.

Optionally, the GUI layout information database of the external device comprises information associated with a location of one or more graphical features to be displayed on the electronic display when operating the surgical device associated with the GUI layout information.

According to an aspect is provided a computer program product, or a non-transitory computer readable storage medium storing one or more programs, comprising software code portions for operating and maintaining a graphical user interface (GUI) layout database, for execution by one or more processors of an electronic device that when executed by the device, causes the device to: receive GUI layout information from a first external device, wherein the GUI layout information comprises identification data that identifies one or more surgical devices associated with the GUI layout information, update a GUI layout database with the received GUI layout information from the external device, receive a request for GUI layout information from a second external device, wherein the received request includes surgical device identifying information, match the received surgical device identifying information to one or more entries in the GUI layout database, and transmit the one or more matching entries in the GUI layout database to the second external device, wherein the second external device is configured to render one or more GUIs in response to determining that it is communicatively coupled to the surgical device, and wherein the GUI is rendered based on the transmitted one or more matching entries in the GUI layout database.

Optionally, the GUI layout information is received from the first external device over a network interface.

Optionally, the GUI layout information comprises information associated with one or more graphical features configured to accept input from a user of a surgical device associated with the GUI layout information.

Optionally, the GUI layout information includes a layout file.

Optionally, the layout file is implemented using JavaScript Object Notation (JSON) format.

Optionally, the layout file is implemented using Extensible Markup Language (XML) format.

Optionally, the GUI layout information includes a library file.

Optionally, the library file is implemented using a Dynamic-link library (DLL).

Optionally, the library file is implemented using a statically linked library.

Optionally, the second external device comprises a controller configured to control and coordinate one or more surgical device used during a surgical procedure.

BRIEF DESCRIPTION OF THE FIGURES

The invention will now be described, by way of example only, with reference to the accompanying drawings, in which.

DETAILED DESCRIPTION

Figure 1:
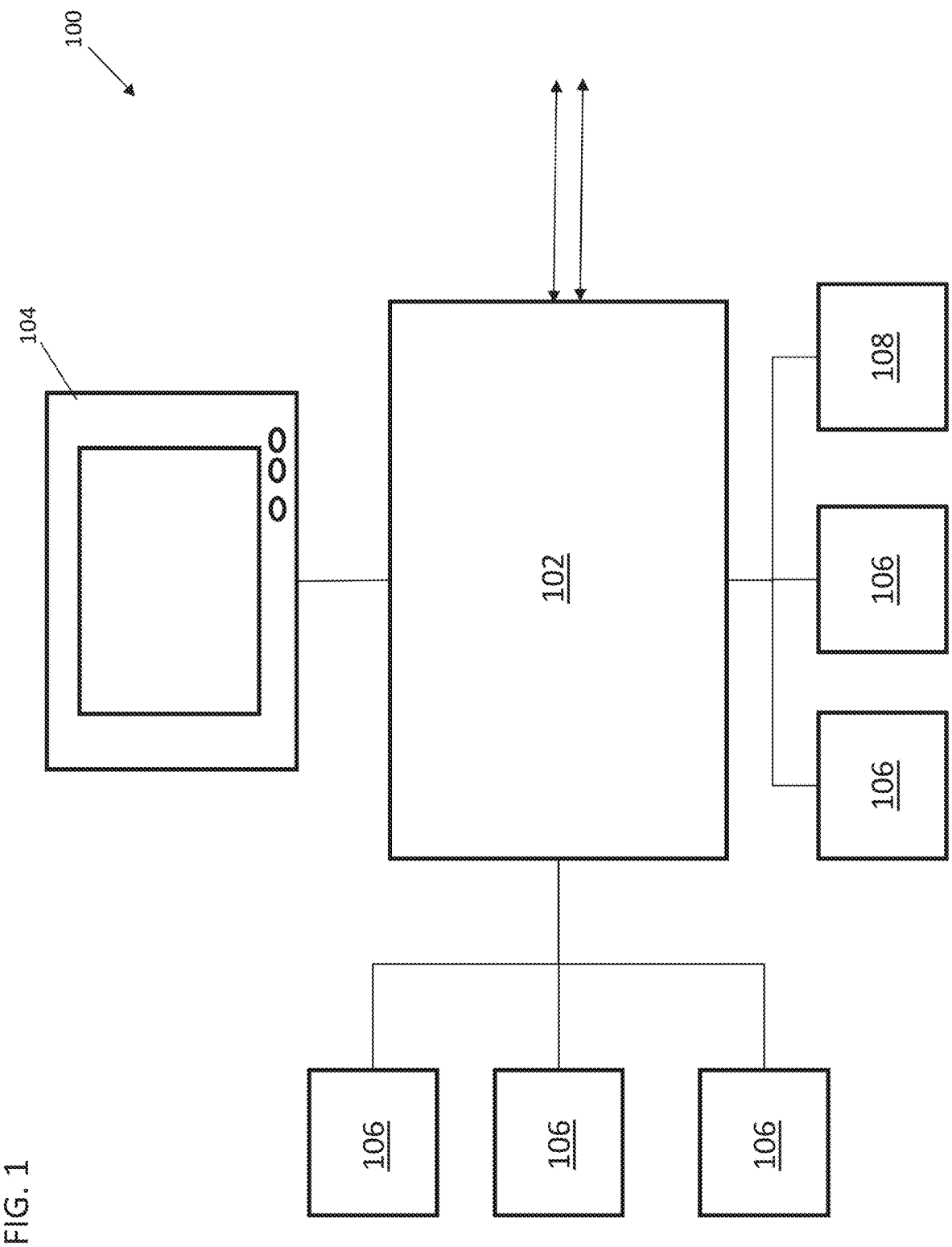
FIG. 1 illustrates an exemplary operating room hub controller system according to example of the disclosure.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are systems and methods for managing and storing graphical user interfaces for medical devices connected to a central controller or hub. According to various examples, a controller (i.e., "hub") can be communicatively coupled to a plurality of peripheral surgical devices, and the hub can further be configured to collectively control and coordinate the operation of each of the devices during a surgical procedure. The hub can maintain an internal GUI database such that when a medical device is connected to the hub, the GUI layout information data corresponding to the device stored in the GUI database can be retrieved and rendered by the hub onto an electronic display. If a device is connected to the hub and a corresponding entry in the GUI database does not exist, the hub can transmit a request to an external GUI database via a network connection for the GUI layout information pertaining to the newly connected device After receiving the request, the external GUI database can transmit the GUI layout information to the hub, and the hub can then store the new layout information in a memory of the hub for later access by the device when needed.

According to an aspect, a device connected to the hub can store its own GUI layout information. When the device is initially connected to the hub, the device can, e.g. automatically, transmit its GUI layout information to the hub, and the hub can store the information in its internal GUI database. The hub can then use the information stored in the GUI database to render the GUI information at an electronic display when needed. The graphical user interface layout information can for example include information associated with the location on a screen of one or more graphical features to be displayed on the electronic display when operating the device associated with the GUI layout information.

In the following description of the various examples, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations described herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs. In one or more examples, the systems and methods presented herein, including the computing systems referred to in the specification may be implemented on a cloud computing and cloud storage platform.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present disclosure as described herein.

A surgeon may make use of numerous tools during a surgical procedure. For instance, a given surgical procedure may require the use of multiple different types of imaging equipment, cutting tools, and other tools such as insufflators, which allow the surgeon to carry out the surgical procedure with greater precision and efficiency. Many tools and equipment used by the surgeon may employ the use of graphical user interfaces (GUIs) as a way for the surgeon to both receive and transmit information to and from each device. In order to have access to the GUI for each device, each device must have access to an electronic display so that it can display its GUIs to the surgeon. Each medical device can have its own electronic display associated with it, however this may not be optimal because it would require multiple display devices to be positioned around the operating environment, and could lead to an increased cognitive load on the surgeon and increase the chance for error. Alternatively, some or all of the devices can share a single display, however in order to view a GUI associated with a particular device, the surgeon or other practitioner may be required to manually switch the video input at the electronic display so that the correct GUI is on the electronic display based on what the surgeon wants at any given time.

The GUIs of the devices can be coordinated using an operating room "hub" controller. In one or more examples, the hub controller can interface with a plurality of devices simultaneously and coordinate access to the GUIs of each device at a single electronic display thereby reducing the cognitive burden on the surgeon. FIG. 1 illustrates an exemplary operating room hub controller system according to examples of the disclosure. The hub controller system 100 can include a hub controller 102 that processes data received from one or more devices 106 to generate one or more display feeds for displaying enhanced medical imaging or graphical user interfaces on one or more displays 104. The one or more devices 106 may generate image data or other data associated with treatment of a patient. The image data can be images or videos generated during treatment of the patient in support of one or more medical procedures, such as video captured by an endoscopic camera during an endoscopic procedure on a patient. Examples of medical imaging modalities include, without limitation, endoscopic systems, open field imaging systems, x-ray systems such as intraoperative c-arm systems, computer tomography systems, ultrasound systems, magnetic resonance imaging systems, and nuclear medicine systems.

The devices 106 can include one or more non-imaging devices that may be used in connection with (e.g., during) a medical imaging session and that may provide information that may be relevant for display during a medical imaging session. Non-limiting examples of non-imaging devices include insufflators, illumination controllers, and voice control systems.

In this example, hub 102 may receive data from the one or more devices 106 that interface with the hub 102 via a wired interface such as through one or more input ports located on the hub 102. The devices 106 can interface with the hub using a wired interface and/or a wireless connection interface such as WiFi, Bluetooth, etc. The hub 102 can generate one or more display feeds using received imaging data and transmits the one or more display feeds to one or more displays 104 via one or more output ports configured to transmit data from the hub 102 to the display 104. In addition to imaging data, the hub 102 can generate one or more display feeds that include GUIs associated with the devices communicatively coupled to the hub 102. In one or more examples, the hub 102 can include input and output ports of various types such as DVI ports, HDMI ports, RS232 ports, IP ports, and the like.

One or more user interfaces 108 may be connected to hub 102 for a user to provide input to the hub 102. The user may input data related for configuring the hub 102 for an imaging session or other surgical procedure. User input can include, for example, selection of a practitioner profile associated with an upcoming medical procedure, selection of a type of medical procedure or types of procedure to be performed during an medical procedure, or any other relevant information. The one or more user interfaces 108 may include a tablet, a keyboard, a mouse, a voice control system, a keypad, a touchscreen, or any combination thereof.

As described in detail below, the hub 102 can render one or more GUIs associated with each of the devices connected to it and can coordinate the presentation of the GUIs at the electronic display so as to facilitate an efficient single display where the surgeon can interact with each of the devices connected to the hub 102. In one or more examples, the hub 102 can combine multiple imaging sources and/or GUIs from different devices into a single display feed, can process received imaging data to generate richer imaging data, can modify imaging data for better utilization of display space, and/or can reconfigure the processing of imaging data depending on the needs and preferences of users from imaging session to imaging session.

Figure 2A:
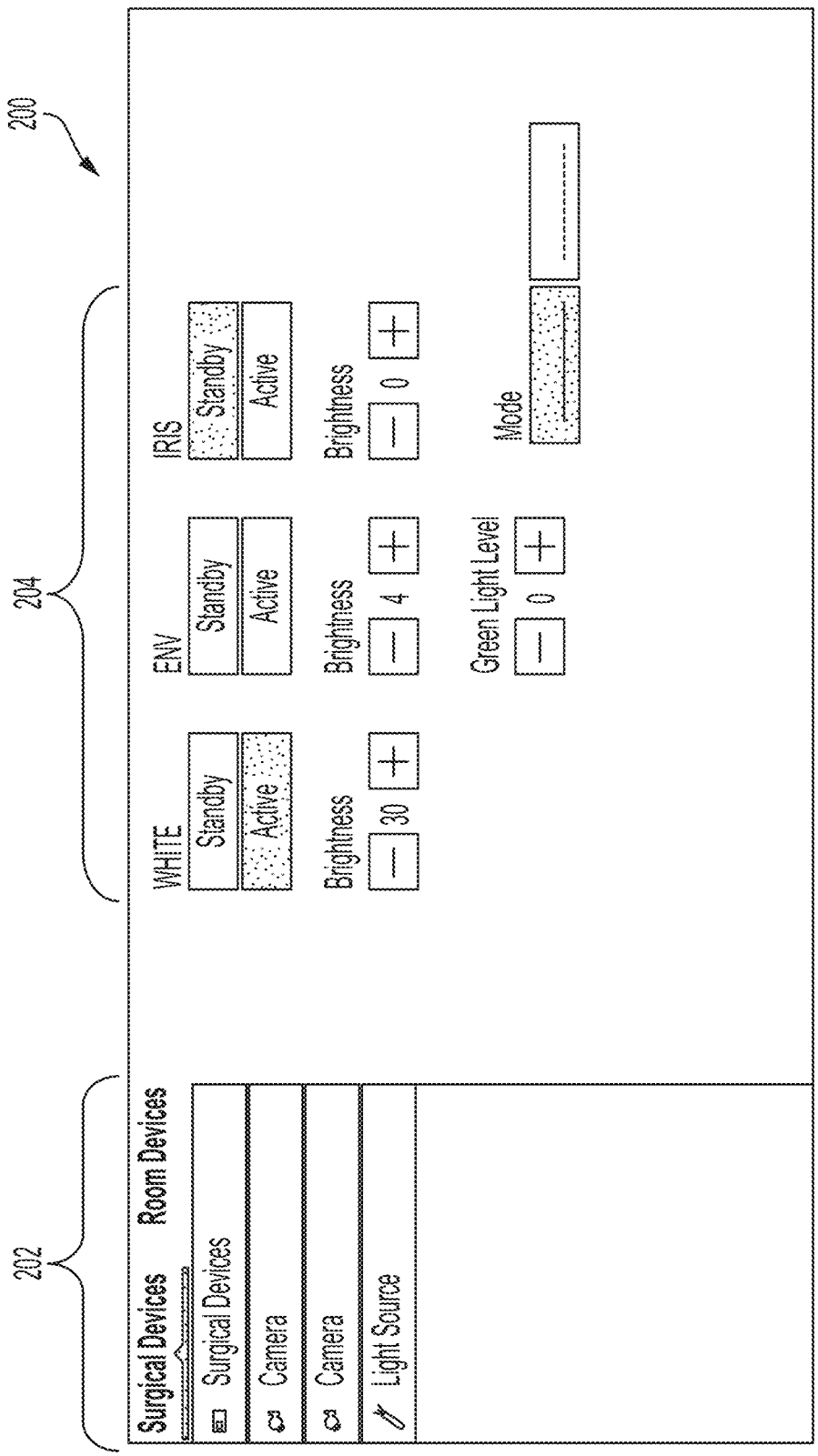
FIG. 2A illustrates an exemplary graphical user interface associated with a device connected to the hub according to examples of the disclosure.

FIG. 2A illustrates an exemplary graphical user interface associated with a device connected to the hub according to examples of the disclosure. The exemplary GUI 200 of FIG. 2A is meant as an example of a graphical user interface that can be rendered and displayed by the hub 102 of FIG. 1. In one or more examples, the GUI 200 of FIG. 2A can be rendered by the hub in a manner that can allow for the user (i.e., a surgeon) to switch between different control and image graphical user interfaces associated with each device without having to manually switch video inputs. In one or more examples, a GUI 200 can include a device selection portion 202 that can be configured to allow for the surgeon to choose which device's GUI to access at any given time. As shown in the example GUI 200, the device selection portion 202 can allow for the surgeon to select various surgical devices, cameras, and light sources that are connected to the hub 102.

When a surgeon makes a selection of a device at device selection portion 202, the one or more GUIs associated with that device can be rendered and displayed at device GUI portion 204 of GUI 200 as illustrated in FIG. 2A. Thus, the GUI displayed at device GUI portion 204 can correspond to the device selected by the user at device selection portion 202. In this way, the surgeon can simply change between GUI's by interfacing with a single GUI rather than having to look at multiple displays or manually change the video input of a single display. In the example of FIG. 2A the GUI illustrated at device GUI portion 204 can include one or more user selectable buttons that can allow the surgeon to toggle or adjust various settings on the device selected at device selection portion 202. The buttons presented to the user can be specific to the device associated with the GUI and the orientation of the buttons on the screen can be configured based on the device associated with the GUI. In this example, and as described in further detail below, each device associated with the hub 102 can have GUI information stored in the hub in the form of a layout file which informs the hub as to the specific user interface elements, such as buttons, and their layout on the screen so that when the surgeon or other user selects a device, the hub can render the corresponding GUI according to that GUI's layout file. Each GUI layout file corresponding to a device connected to the hub can be in one or more file formats such as Extensible Markup Language (XML) and JavaScript Object Notation (JSON) and can include an associated library file (dll, lib, so, etc) and any other files needed to render the GUI and to send control singles from the GUI back to a device via the hub.

Figure 2B:
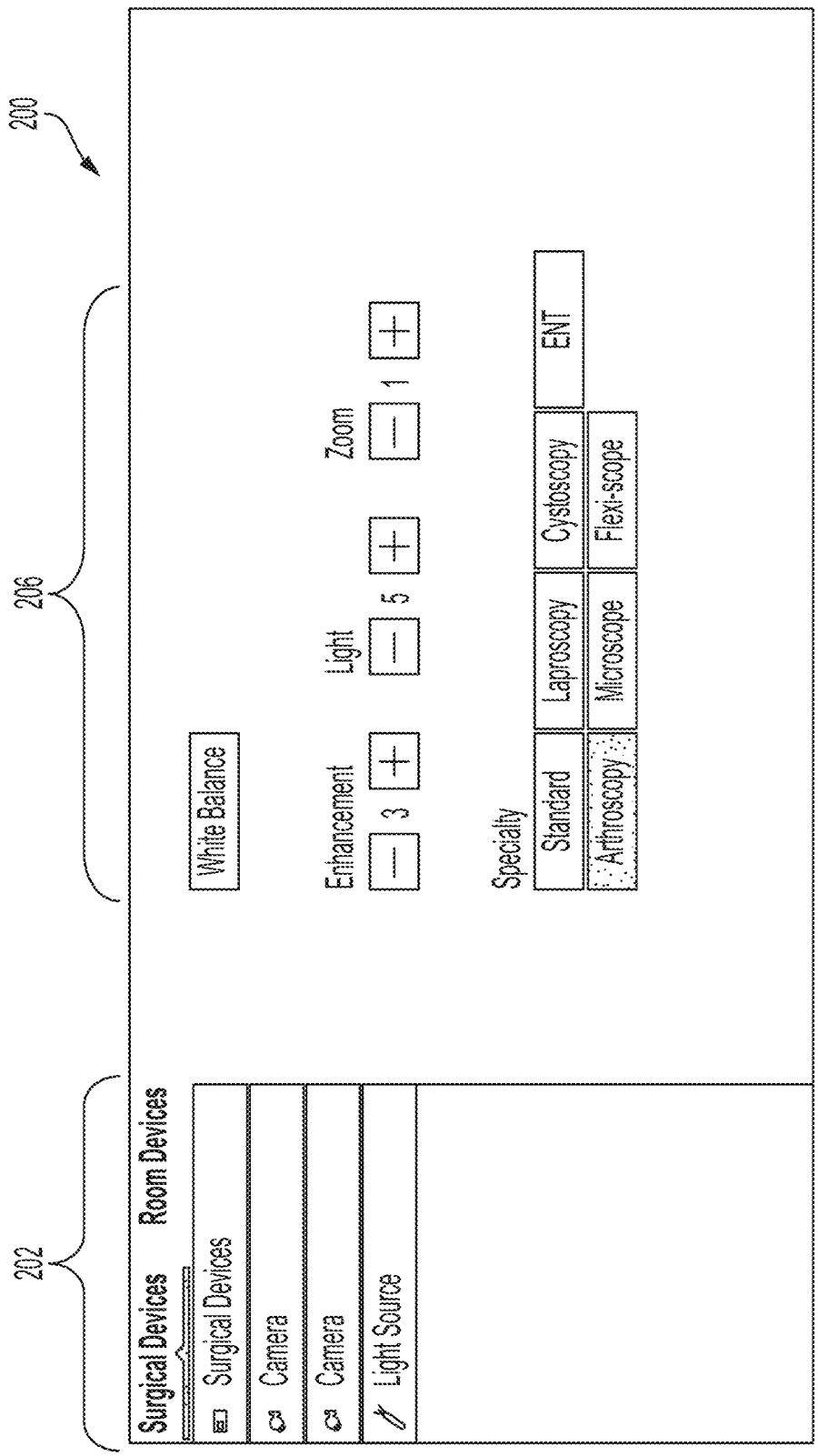
FIG. 2B illustrates another exemplary graphical user interface associated with a device connected to the hub according to examples of the disclosure.

As discussed above, each device connected to the hub can have a layout file associated with it that is unique to the device and can be specifically configured to include features and images associated with the device. FIG. 2B illustrates another exemplary graphical user interface associated with a device connected to the hub according to examples of the disclosure. As shown in FIG. 2B, if the surgeon selects a new device from device selection portion 202, a new GUI can be displayed at device GUI portion 204 of GUI 202 that is associated with the device selected by the surgeon. As shown in FIGS. 2A and 2B (by the differences in GUI portion 204) each device can have a unique interface that is presented to the surgeon. The details of the interface can be stored in the layout file as described above.

In one or more examples, the hub 102 of FIG. 1 can include a processor and a memory. In one or more examples, the memory can store a software program that when executed by the processor carries out the functions of the hub 102 such as rendering GUIs based upon the device selected by the surgeon as described above with respect to FIG. 2. In one or more examples, the GUI layout files associated with each device that can be connected to the hub at any given time can be stored in the memory as part of the software program that is used by the processor to operate the hub 102. Since the hub 102 is a medical device that can be used during a surgical procedure, it may be subject to regulatory verification and approval before it can be deployed into an operating theatre or other medical environment, and be used to assist in medical procedures. The software that is used to operate the hub can also be subject to the regulatory verification and approval process to ensure that the software does not have operational issues that may compromise the safety of any given medical procedure in which the hub is involved. The process of obtaining regulatory approval for the hub and its associated software can be long and cumbersome. In one or more examples, verifying the software of the entire hub can take months, as the hub, in addition to the GUI layout files, can include software designed to interact with the devices connected to the hub often sending commands to each device from and receiving operation data about each device at the hub.

In one or more examples, a given version of the software used to operate the hub can be initially loaded on the hub device and contain all of the known GUI layout files for devices that could possibly be connected with the hub. However, if a new medical device comes online or becomes available after the software on the hub has been loaded and is operational, the new device may not be able to be operated by the hub since the software loaded on the hub may not include a GUI layout file associated with the new device. In order to make the new device operational with the hub, the software loaded onto the hub may have to be updated (i.e., removed and replaced with a new software file) that includes GUI layout information for the new device. However, because the software on the hub is subject to the regulatory verification and approval process, updating the software may not be possible until the updated software with the new GUI layout file for the new device has independently gone through the regulatory process. This can mean that adding a single new device to the devices that can connect to the hub, can engender a months long regulatory process, which can frustrate the ability of the hub to be updated on a regular basis.

In order to efficiently update the GUI layout information stored on the hub to accommodate new devices, in one or more examples, the hub can be configured such that the GUI layout information associated with new and existing devices of the hub can be "de-coupled" from the software used to operate on the hub. In other words, the hub system can be configured such that the GUI layout information can be modified and updated (i.e., for new devices) without requiring that the entire software used to operate the hub be updated. While in or more examples, the new GUI layout files to be added to the hub may still have to undergo a regulatory verification and approval process, since the layout files are not as complex and large as the overall software that is used to operate the hub, the process may be shorter in length and less cumbersome, thus allowing the GUI layout files stored on a hub to be updated on a regular basis and thus allowing the hub to be able to keep up with new devices that may become available for connection with the hub.

Figure 3:
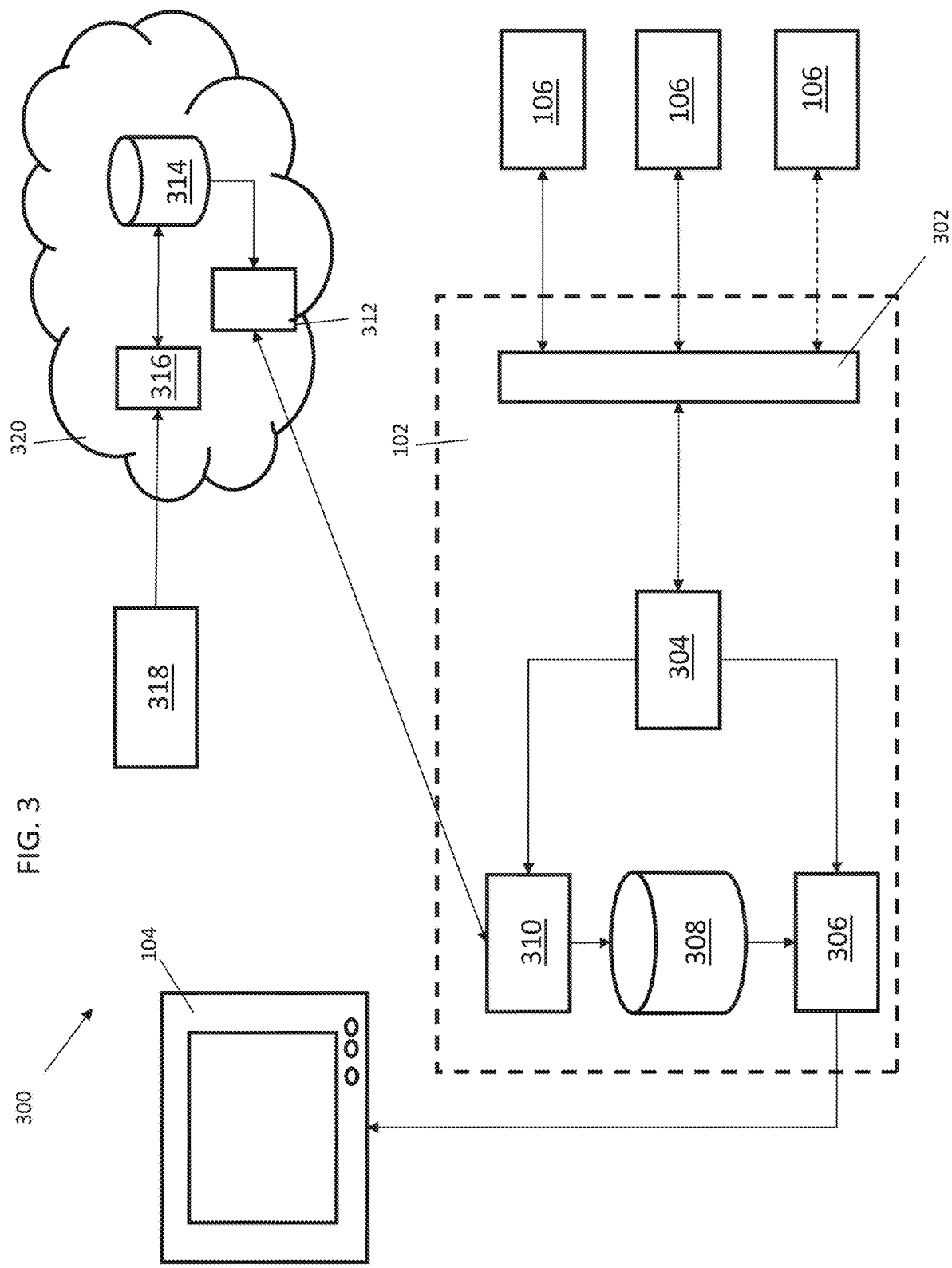
FIG. 3 illustrates an exemplary system for updating and maintaining graphical user interface layout information according to examples of the disclosure.

FIG. 3 illustrates an exemplary system for updating and maintaining graphical user interface layout information according to examples of the disclosure. In one or more examples, the system 300 of FIG. 3 can be configured to allow for a hub 102 to update the GUI layout files stored in the hub without requiring the hub to replace its operational software each time a new GUI layout file is to be added. In one or more examples, the system 300 includes a hub 102 that is communicatively coupled to one or more medical devices 106 (i.e., surgical peripherals) as described above with respect to FIG. 1. In one or more examples, the medical devices 106 can be communicatively coupled to the hub 102 via an interface unit 302. In one or more examples, the interface unit 302 can be configured to receive data from the medical devices 106 at the hub, and can be configured to transmit data from the hub 102 to the medical devices 106. In one or more examples, the interface unit can convert application data generated by the hub into data formatted in a specific communications protocol used to facilitate communications between the hub 102 and the medical devices 106.

In one or more examples, the hub 102 of system of system 300 can include a device management unit 304. In one or more examples, the device management unit 304 can receive the data from each device, and process it so as to operate the hub 102 based on the data collectively received from the medical devices 106. In one or more examples, each device 106 connected to the hub 102, when initially connected to the hub, can transmit device identification information to the hub which can be received at device management unit 304 via the interface unit 302. In one or more examples, the device identification information can be used by the device management unit 304 can be used coordinate the GUI's presented to the display 104 based on which devices 106 are connected to the hub 102. In one or more examples, and as described in further detail below, the device management unit 304 can use the device identification information received from each device to retrieve one or more GUI layout information files associated with the devices, so as to render the appropriate GUIs on the display 104, based on the identification of the device or devices communicatively coupled to the hub 102 at any given time.

In one or more examples, the hub 102 can include a GUI render engine 306 that is configured to render one or more GUIs on the electronic display based on the identities of the devices 106 connected to hub 102. In one or more examples, the GUI render engine 306 can be configured to convert GUI layout information (described above) associated with each device identified as being connected to the hub into one or more GUIs that are displayed on the electronic display 104. In one or more examples, the GUI render engine 306 can use the device identifying information provided to it by device management unit 304 to retrieve one or more GUI layout information files from a GUI layout information database 308. In one or more example, GUI layout information database 308 can contain a plurality of entries, with each entry in the database associated with a GUI of a particular device that can be connected to the hub. In one or more examples, a first entry of the database can include the device identification number associated with a camera, and the GUI layout information of that camera. In one or more examples, when the GUI render engine 306 receives device identifying information (i.e., device ID) corresponding to the camera, the GUI render engine 306 can query the database 308 to search for all entries that correspond to a camera with the same device ID. All matching entries, once found, can be transmitted to the GUI render engine 306 for rendering on the electronic display 104.

In one or more examples, if an entry in the GUI layout information database 308 that matches a specific device identification number cannot be found (for instance if a new device is connected to the hub) then in one or more examples the GUI render engine 306 can transmit a notification to the device management unit 304, letting it know that the GUI layout information database 308 does not contain GUI layout information for the device corresponding to the device identification number. Once notified that the GUI layout information database 308 does not contain an entry corresponding to the device, in one or more examples, the device management unit 304 can initiate a process to download the GUI layout information corresponding to the device from an external device (as described in further detail below).

In one or more examples, if a corresponding entry is not found in the GUI layout information databased 308, then the data management unit 304 can transmit a request to a local database update client 310 that is configured to access one or more external devices so as to download the needed GUI layout information and add it to the GUI layout information database 308 of the hub 102. In one or more examples, the database update client 310 in addition to retrieving and downloading GUI layout information for new devices can also be configured to download updated GUI layout information for devices that already have GUI layout information entries in the local database 308 of the hub 102.

In one or more examples, the database update client 310 can contact an external device 320 to download GUI layout information that the hub 102 does not possess or information that needs to be updated. In one or more examples, the external device 320 can be located in a separate location from the hub 102 and can be accessed by the database update client 310 using a networked connection such as the internet. In one or more examples, the external device 320 can be accessible by multiple hub devices located in different locations and can act as a central repository of GUI layout information that can be accessed by any hub connected to it via a network so as to update or download GUI layout information. In one or more examples, the external device 320 can be implemented as a cloud-based device. Alternatively in one or more examples, the external device 320 can be implemented using a server or other computing system that can be configured to store GUI layout information and transmit the information to requesting hubs.

In one or more examples, the external device 320 (i.e., the GUI layout information repository) can include its own GUI layout information database 314 similar to the GUI layout information database 306 located internally within each hub. Thus, the GUI layout information database 314 of the external device 320 can include entries associated with specific devices and versions of devices that can be connected to a hub. In one or more examples, each entry in the GUI layout information database 314 can include device identification information (identifying the device that corresponds to the GUI layout information) and corresponding components needed by a control system to produce GUIs for a device which may include a layout file (XML, JSON, etc), associated library file (dl, lib, so, etc) and any other files needed to render GUIs and to send control signals from a GUI back to a device. The GUI layout information database 314 of device 320 can include layout information for different version of device software and for different kinds of displays corresponding to a single device.

In one or more examples, the external device can include a web interface server 316 that is configured to allow for adding/removing layout information to/from the database 314 through a web browser. Thus, in one or more examples, the GUI layout information database can be updated using a computing device 318 that accesses the database 314 via a web browser and that can connect with the external device 320 via the web interface 316. In this way, an authorized user, can continuously update the GUI layout information database 314 of the external device 320, and that updated information can be accessed by a hub when the hub requests updated or new information from the external device (for instance when a unrecognized device is initially connected to the hub).

In one or more examples, the external device can include a database read only server 312 that can allow for hubs to fetch layout information for the requested device using that device's unique identifier. In one or more examples, the hub 102 can transmit the unique identifier of a device via its update client 310 to the database read only server 312. Upon receipt of the unique identifier from the hub 102, the database read only server 312 can retrieve GUI layout information from the GUI layout information database 314 using the unique identifier provided by the hub. In one or more examples, the database read only server 312 can be configured to have only read access to the database 314 so as to prevent malicious users or hubs from altering the contents of the database 314. In this way, the only mechanism to update the database 314 is via the web interface 316, which can include security features to ensure that only authorized users are allowed to update the database 314.

The system 300 described above with respect to FIG. 3 can allow for GUI layout information to be updated at a hub without requiring the entire software that is used to operate the hub to be replaced. Thus, anytime GUI layout information is added or updated at the external device, the layout information itself can go through the validation process rather than the software that is used to operate the hub. By "de-coupling" the GUI layout information from the software used to operate the hub, the frequency of software updates can be reduced, and the validation process required to update GUI layout information can be made simpler and more efficient since it is isolated to each GUI layout information file rather than requiring validation of the entire software package. In one or more examples, the process of updating the external device and pushing new GUI layout information files to various hubs can be verified and validated prior to initial rollout to ensure that the process itself complies with regulatory requirements. Thus, when a new GUI layout information file is added, the only validation that may be required is to validate the new file and not any of the processes associated with pushing the new layout file to a hub.

Figure 4:
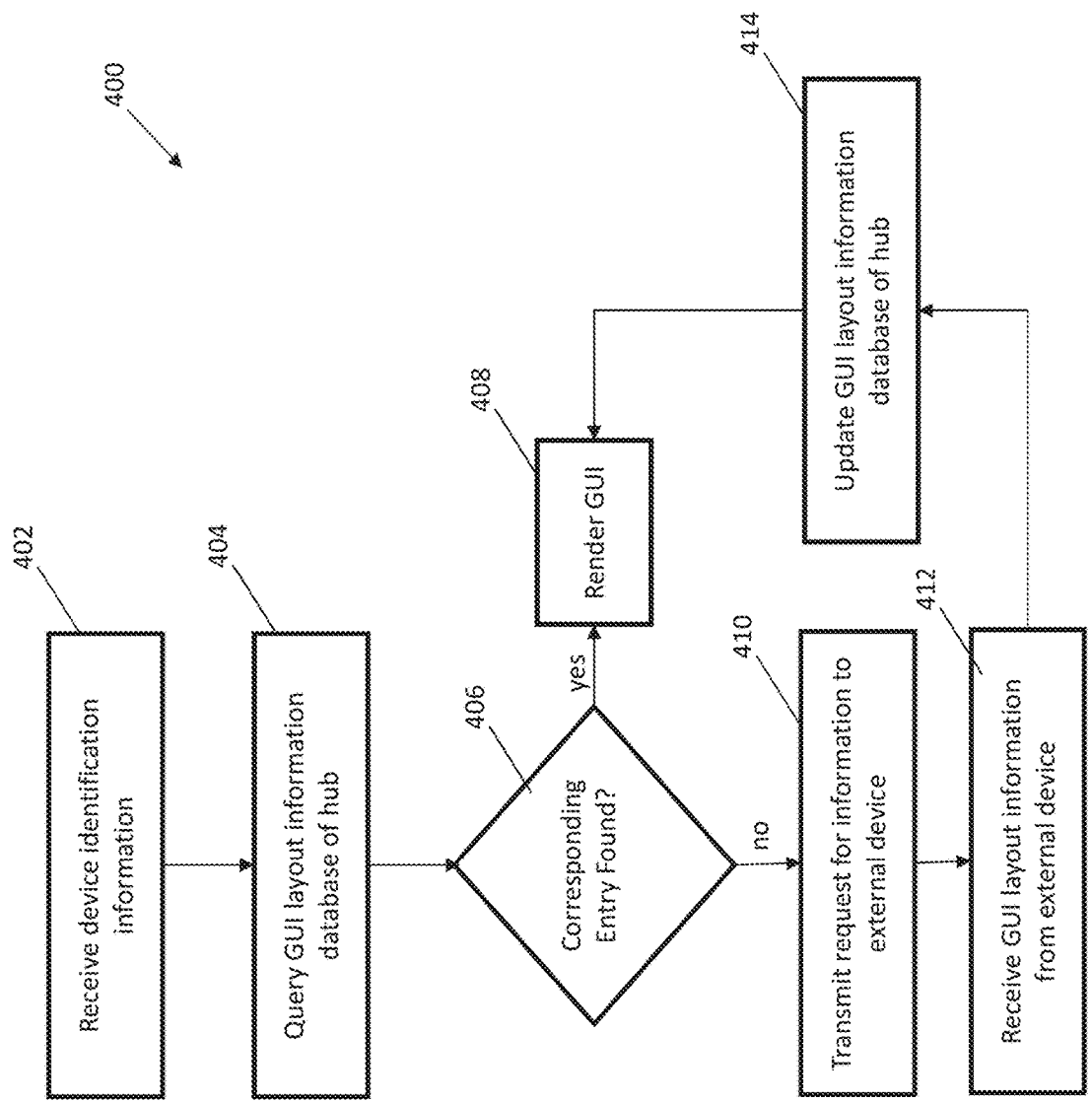
FIG. 4 illustrates an exemplary process for updating graphical user interface layout information at a hub according to examples of the disclosure.

FIG. 4 illustrates an exemplary process for updating graphical user interface layout information at a hub according to examples of the disclosure. In one or more examples, the process 400 of FIG. 4 can be executed by a hub 120 working in conjunction with one or more medical devices 106 and one or more external devices 320. In one or more examples, the process 400 of FIG. 4 can begin at step 402 wherein the hub 102 received device identification information from a medical device 106 that is communicatively coupled to the hub 102. In one or more examples, when a medical device is initially connected to the hub, the device can be configured to automatically transmit device identification information to the hub. In one or more examples, device identification information can include a device identification number or code that is unique for each medical device that is capable of being connected to the hub. In one or more examples, upon being connected to the hub 102, a medical device 106 can automatically transmit the device identification number to the hub 102, or alternatively at step 402, the hub 102 can transmit a request for identification to the medical device once it detects that the device has been connected to the hub.

In one or more examples, once the hub 102 receives the device identification information at step 402, the process 400 can move to step 404 wherein the hub 102 can use the device identification information received at step 402 to query an internal GUI layout information database that is located internally in the hub 102 (e.g., GUI layout information database 308). In one or more examples, querying the database can include finding entries in the GUI layout information database 308 that match the device identification information received at the hub 102 at step 402. After querying the database at step 404, the process 400 can move to step 406 wherein a determination is made as to whether the database includes any matching entries. If a matching entry is found at step 406, then the process 400 can move to step 408 wherein the hub proceeds to use the layout information stored at the matching entry to render a GUI that corresponds to the device information received at step 402.

In one or more examples, if a corresponding entry is not found at step 406, then the process 400 can move to step 410 wherein the hub 102 transmits a request to an external device for GUI layout information corresponding to the device identification information received at step 402. In one or more examples, the request can be sent using one or more networked connection mediums (i.e., wired or wireless) and using one or more communication protocols such as TCP/IP, etc. As described above with respect to the example of FIG. 3, the external device can store GUI layout information for all known devices that can be connected to the hub, and can be updated periodically by an authorized user. Also as described above, the external device can be configured so that it can communicate with multiple hubs simultaneously and field requests for GUI layout information that each hub may not have stored internally at the hub itself.

In one or more examples, after transmitting a request for GUI layout information at step 410, the hub 102 can subsequently receive the requested GUI layout information at step 412 from the external device. Once the information is received at step 412, the process 400 can move to step 414 wherein the GUI layout information database located internally within the hub can be updated using the information received from the external device. Once the database has been updated at step 414, the process 400 can then proceed to step 408 wherein a GUI is rendered based on the information stored in the GUI layout information database of the hub.

In one or more examples, the system 300 of FIG. 3 can also be configured to receive GUI layout information directly from a medical device plugged into the hub, rather than having to access another external device that stores GUI layout information, to retrieve one or more GUIs corresponding to the device. In a system, in which a device stores its own GUI layout information, when the device is plugged into the hub for the first time, then the device can transmit its GUI layout information to the hub, and that information can be used to update the hub's GUI layout information database. Such a system can minimize the number of times that the hub has to contact an external device to retrieve GUI layout information that it doesn't already have stored internally.

Figure 5:
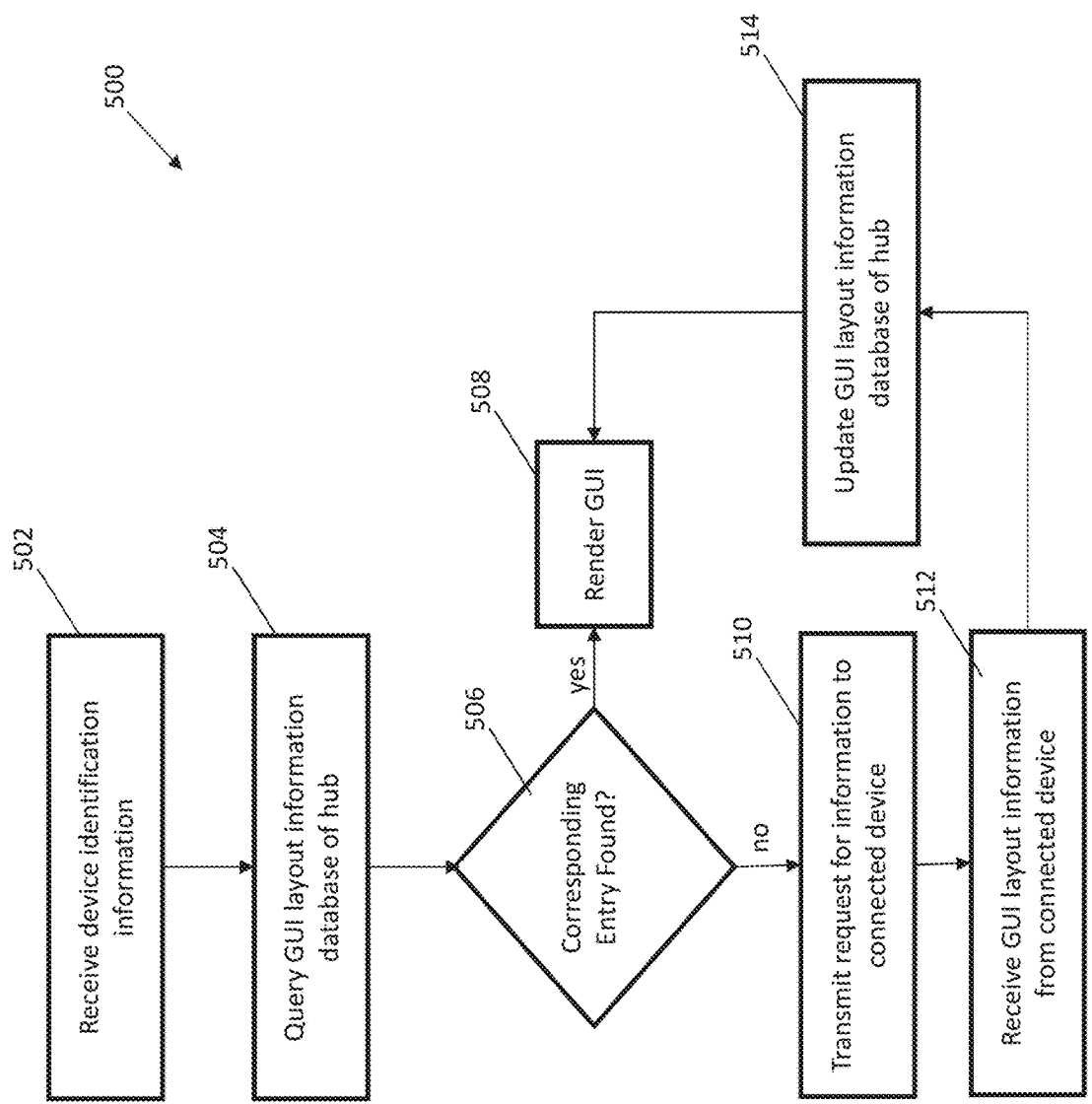
FIG. 5 illustrates another exemplary process for updating graphical user interface layout information at a hub according to examples of the disclosure.

FIG. 5 illustrates another exemplary process for updating graphical user interface layout information at a hub according to examples of the disclosure. In one or more examples, the process 500 of FIG. 5 can be executed by a hub 120 working in conjunction with one or more medical devices 106. In one or more examples, the process 500 of FIG. 5 can begin at step 502 wherein the hub 102 received device identification information from a medical device 106 that is communicatively coupled to the hub 102. In one or more examples, when a medical device is initially connected to the hub, the device can be configured to automatically transmit device identification information to the hub. In one or more examples, device identification information can include a device identification number or code that is unique for each medical device that is capable of being connected to the hub. In one or examples, upon being connected to the hub 102, a medical device 106 can automatically transmit the device identification number to the hub 102, or alternatively at step 502, the hub 102 can transmit a request for identification to the medical device once it detects that the device has been connected to the hub.

In one or more examples, once the hub 102 receives the device identification information at step 502, the process 500 can move to step 504 wherein the hub 102 can use the device identification information received at step 502 to query an internal GUI layout information database that is located internally in the hub 102 (e.g., GUI layout information database 308). In one or more examples, querying the database can include finding entries in the GUI layout information database 308 that match the device identification information received at the hub 102 at step 502. After querying the database at step 504, the process 400 can move to step 506 wherein a determination is made as to whether the database includes any matching entries. If a matching entry is found at step 506, then the process 500 can move to step 508 wherein the hub proceeds to use the layout information stored at the matching entry to render a GUI that corresponds to the device information received at step 502.

In one or more examples, if a corresponding entry is not found at step 506, then the process 500 can move to step 510 wherein the hub can transmit a request for GUI layout information from the medical device itself. In one or more examples, rather than attempting to contact an external device (i.e., a repository) to find missing GUI information, the medical device itself can store the GUI layout information. In one or more examples, at step 510, the hub after recognizing that it doesn't have GUI layout information corresponding to the device stored in its own internal GUI layout information database, can send a request to the device for it to transmit its own GUI layout information that is stored in a memory located within the medical device. In one or more examples, the device can transmit its own GUI layout information in response to the request, wherein the request is received by the hub at step 512. Once the information is received at step 510, the received information can be used to update the GUI layout information database of the hub at step 514. Once the database has been updated at step 514, the process 500 can then proceed to step 508 wherein a GUI is rendered based on the information stored in the GUI layout information database of the hub.

As illustrated by the systems and methods described above in FIGS. 3-5, a hub can be configured to adapt to new devices without having to update or replace the software on the device. By avoiding software updates, the burdens of time and effort spent validating software can be minimized. Since the software that operates a hub may include both GUI software as well as software that operates the hub, a system that requires full software updates to accommodate new GUIs associated with new devices may not be ideal. Instead, by de-coupling the GUI layout information from the software using the systems and methods described above, any changes or additions to GUIs do not require an update of the entire software running on the hub.

Figure 6:
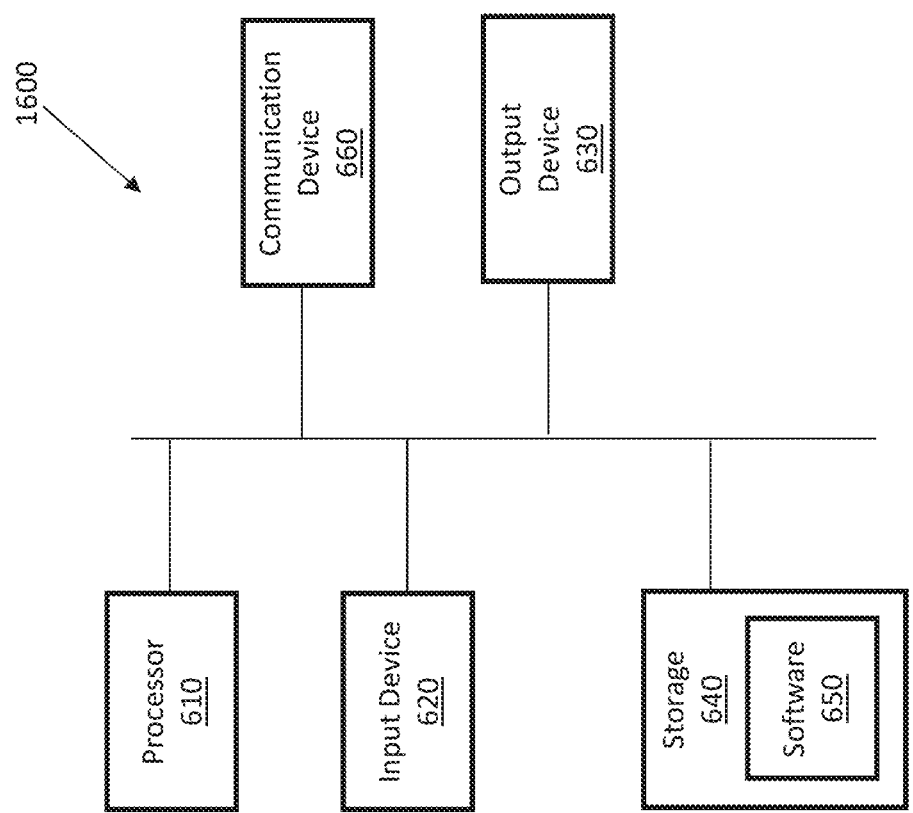
FIG. 6 illustrates an exemplary computing system, according to examples of the disclosure.

FIG. 6 illustrates an example of a computing system 600, in accordance with some examples, that can be used for one or more components of system 100 of FIG. 1. System 600 can be a computer connected to a network, such as one or more networks of hospital, including a local area network within a room of a medical facility and a network linking different portions of the medical facility. System 600 can be a client or a server. As shown in FIG. 6, system 600 can be any suitable type of processor-based system, such as a personal computer, workstation, server, handheld computing device (portable electronic device) such as a phone or tablet, or dedicated device. The system 600 can include, for example, one or more of input device 620, output device 630, one or more processors 610, storage 640, and communication device 660. Input device 620 and output device 630 can generally correspond to those described above and can either be connectable or integrated with the computer.

Input device 620 can be any suitable device that provides input, such as a touch screen, keyboard or keypad, mouse, gesture recognition component of a virtual/augmented reality system, or voice-recognition device. Output device 630 can be or include any suitable device that provides output, such as a display, touch screen, haptics device, virtual/augmented reality display, or speaker.

Storage 640 can be any suitable device that provides storage, such as an electrical, magnetic, or optical memory including a RAM, cache, hard drive, removable storage disk, or other non-transitory computer readable medium. Communication device 660 can include any suitable device capable of transmitting and receiving signals over a network, such as a network interface chip or device. The components of the computing system 600 can be connected in any suitable manner, such as via a physical bus or wirelessly.

Processor(s) 610 can be any suitable processor or combination of processors, including any of, or any combination of, a central processing unit (CPU), field programmable gate array (FPGA), application-specific integrated circuit (ASIC), and a graphical processing unit (GPU). Software 650, which can be stored in storage 640 and executed by one or more processors 610, can include, for example, the programming that embodies the functionality or portions of the functionality of the present disclosure (e.g., as embodied in the devices as described above).

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 600 can implement any operating system suitable for operating on the network. Software 650 can be written in any suitable programming language, such as C, C++, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated. For the purpose of clarity and a concise description, features are described herein as part of the same or separate examples; however, it will be appreciated that the scope of the disclosure includes examples having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for controlling a surgical device connected to a surgical hub comprising:
   receiving first data from a surgical device communicatively coupled to the surgical hub;
   identifying the surgical device based on the received first data;
   querying a database stored in a memory of the surgical hub to determine whether the database includes graphical user interface (GUI) layout information associated with the identified surgical device, wherein the GUI layout information comprises graphical controls specific to the connected surgical device;
   in response to the determination that the database does not include GUI layout information associated with the identified surgical device:
      transmitting a request to an external device for the GUI layout information associated with the identified device;
      receiving the requested GUI layout information from the external device;
      updating the database stored in the memory of the surgical hub with the received GUI layout information; and
      rendering a GUI at an electronic display of the surgical hub based on the received GUI layout information from the external device;
   receiving second data generated by the surgical device; and
   generating at least one display feed based on the second data generated by the surgical device for display on at least one of the electronic display of the surgical hub and at least one external display.

2. The method of claim 1, wherein the first data received from the surgical device communicatively coupled to the surgical hub comprises version information associated with software running on the surgical device.

3. The method of claim 1, wherein the database comprises a plurality of entries associated with the surgical device, wherein each entry of the database is associated with a version of the software running on the surgical device.

4. The method of claim 1, wherein the GUI layout information comprises information associated with a location on the electronic display of one or more graphical features to be displayed when operating the device associated with the GUI layout information.

5. The method of claim 1, wherein the GUI layout information comprises information associated with one or more graphical features configured to accept input from a user of the surgical device associated with the GUI layout information.

6. The method of claim 1, wherein the GUI layout information includes a layout file.

7. The method of claim 1, wherein the external device is implemented on a cloud-based computing device.

8. The method of claim 7, wherein the external device includes a GUI layout information database.

9. The method of claim 1, wherein the received requested GUI layout information is associated with the surgical device communicatively coupled to the surgical hub.

10. The method of claim 9, wherein the GUI layout information database of the external device comprises information associated with a location on the electronic display of one or more graphical features to be displayed when operating the surgical device associated with the GUI layout information.

11. The method of claim 1, wherein the second data generated by the surgical device comprises imaging data.

12. A system for controlling a surgical device connected to a surgical hub, the system comprising:
a memory;
one or more processors;
wherein the memory stores one or more programs that when executed by the one or more processors, cause the one or more processors to:
receive first data from a surgical device communicatively coupled to the surgical hub;
identify the surgical device based on the received first data;
query a database stored in a memory of the surgical hub to determine whether the database includes graphical user interface (GUI) layout information associated with the identified surgical device, wherein the GUI layout information comprises graphical controls specific to the connected surgical device;
in response to the determination that the database does not include GUI layout information associated with the identified surgical device:
transmit a request to an external device for the GUI layout information associated with the identified device;
receive the requested GUI layout information from the external device;
update the database stored in the memory of the surgical hub with the received GUI layout information; and
render a GUI at an electronic display of the surgical hub based on the received GUI layout information from the external device;
receive second data generated by the surgical device; and
generate at least one display feed based on the second data generated by the surgical device for display on at least one of the electronic display of the surgical hub and at least one external display.

13. The system of claim 12, wherein the first data received from the surgical device communicatively coupled to the surgical hub comprises version information associated with software running on the surgical device.

14. The system of claim 13, wherein the database comprises a plurality of entries associated with the surgical device, wherein each entry of the database is associated with a version of the software running on the surgical device.

15. The system of claim 12, wherein the GUI layout information comprises information associated with a location on the electronic display of one or more graphical features to be displayed when operating the device associated with the GUI layout information.

16. The system of claim 12, wherein the GUI layout information comprises information associated with one or more graphical features configured to accept input from a user of the surgical device associated with the GUI layout information.

17. The system of claim 12, wherein the GUI layout information includes a layout file.

18. The system of claim 12, wherein the external device is implemented on a cloud-based computing device.

19. The system of claim 12, wherein the external device includes a GUI layout information database.

20. The method of claim 1, wherein the received requested GUI layout information is associated with the surgical device communicatively coupled to the surgical hub.

21. The method of claim 20, wherein the GUI layout information database of the external device comprises information associated with a location on the electronic display of one or more graphical features to be displayed when operating the surgical device associated with the GUI layout information.

22. The system of claim 12, wherein the second data generated by the surgical device comprises imaging data.

23. A non-transitory computer readable storage medium storing one or more programs for controlling a surgical device connected to a surgical hub, for execution by one or more processors of an electronic device that when executed by the device, causes the device to:
receive first data from a surgical device communicatively coupled to the surgical hub;
identify the surgical device based on the received first data;
query a database stored in a memory of the surgical hub to determine whether the database includes graphical user interface (GUI) layout information associated with the identified surgical device, wherein the GUI layout information comprises graphical controls specific to the connected surgical device;
if the memory in response to the determination that the database does not include GUI layout information associated with the identified surgical device:
transmit a request to an external device for the GUI layout information associated with the identified device;
receive the requested GUI layout information from the external device;
update the database stored in the memory of the surgical hub with the received GUI layout information; and
render a GUI at an electronic display of the surgical hub based on the received GUI layout information from the external device;
receive second data generated by the surgical device; and
generate at least one display feed based on the second data generated by the surgical device for display on at least one of the electronic display of the surgical hub and at least one external display.

24. The non-transitory computer readable storage medium of claim 23, wherein the first data received from the surgical device communicatively coupled to the surgical hub comprises version information associated with software running on the surgical device.

25. The non-transitory computer readable storage medium of claim 24, wherein the database comprises a plurality of entries associated with the surgical device, wherein each entry of the database is associated with a version of the software running on the surgical device.

26. The non-transitory computer readable storage medium of claim 23, wherein the GUI layout information comprises information associated with a location on the electronic display of one or more graphical features to be displayed when operating the device associated with the GUI layout information.

27. The non-transitory computer readable storage medium of claim 23, wherein the GUI layout information comprises information associated with one or more graphical features configured to accept input from a user of the surgical device associated with the GUI layout information.

28. The non-transitory computer readable storage medium of claim 23, wherein the GUI layout information includes a layout file.

29. The non-transitory computer readable storage medium of claim 23, wherein the external device is implemented on a cloud-based computing device.

30. The non-transitory computer readable storage medium of claim 23, wherein the external device includes a GUI layout information database.

31. The non-transitory computer readable storage medium of claim 23, wherein the received requested GUI layout information is associated with the surgical device communicatively coupled to the surgical hub.

32. The non-transitory computer readable storage medium of claim 31, wherein the GUI layout information database of the external device comprises information associated with a location on the electronic display of one or more graphical features to be displayed when operating the surgical device associated with the GUI layout information.

33. The non-transitory computer-readable storage medium of claim 23, wherein the second data generated by the surgical device comprises imaging data.

* * * * *